United States Patent
Chavez et al.

(10) Patent No.: US 8,137,304 B2
(45) Date of Patent: Mar. 20, 2012

(54) MEDICATION DELIVERY DEVICE

(75) Inventors: Enrico Chavez, Morges (CH); Sandrine Piotelat, Faucigny (FR); Vincent Pongpairochana, La Conversion (CH)

(73) Assignee: Ares Trading SA, Aubonne (CH)

( * ) Notice: Subject to any disclaimer, the term of this patent is extended or adjusted under 35 U.S.C. 154(b) by 611 days.

(21) Appl. No.: 11/884,006

(22) PCT Filed: Jan. 27, 2006
(Under 37 CFR 1.47)

(86) PCT No.: PCT/IB2006/000135
§ 371 (c)(1),
(2), (4) Date: May 18, 2009

(87) PCT Pub. No.: WO2006/085175
PCT Pub. Date: Aug. 17, 2006

(65) Prior Publication Data
US 2009/0318878 A1  Dec. 24, 2009

(30) Foreign Application Priority Data

Feb. 14, 2005 (EP) .................................. 05003110
Jan. 13, 2006 (EP) .................................. 06000693

(51) Int. Cl.
*A61M 31/00* (2006.01)
(52) U.S. Cl. ............... 604/67; 604/65; 604/66; 604/207
(58) Field of Classification Search .............. 604/65–67, 604/207–210
See application file for complete search history.

(56) References Cited

U.S. PATENT DOCUMENTS

| 5,928,197 | A | 7/1999 | Niehoff et al. |
| 5,928,201 | A | 7/1999 | Poulsen et al. |
| 6,340,357 | B1 | 1/2002 | Poulsen et al. |
| 6,423,035 | B1 | 7/2002 | Das et al. |
| 7,966,051 | B2 * | 6/2011 | Xie et al. ...................... 600/317 |
| 2002/0151855 | A1 | 10/2002 | Douglas et al. |
| 2004/0092877 | A1 | 5/2004 | Langley et al. |
| 2004/0210199 | A1 * | 10/2004 | Atterbury et al. ............. 604/224 |
| 2005/0029277 | A1 | 2/2005 | Tachibana |

FOREIGN PATENT DOCUMENTS

| DE | 38 24 217 A1 | 1/1990 |
| EP | 1 433 456 A | 6/2004 |
| WO | WO 2005/077441 A2 | 8/2005 |

* cited by examiner

*Primary Examiner* — Bhisma Mehta
*Assistant Examiner* — Larry R Wilson
(74) *Attorney, Agent, or Firm* — Bacon & Thomas, PLLC

(57) ABSTRACT

The medication delivery device is designed to receive a replaceable medication container and to determine an adjusted medication dose AD before each delivery of the medication contained in the medication container if the current content of the medication container is not a multiple of a prescribed dose D and is greater than the prescribed dose D. The adjusted medication dose AD is the dose to be delivered instead of the prescribed dose D during said medication delivery. The adjusted medication dose AD is determined by selecting one of a first dose, to that is higher than the prescribed dose D, and of a second dose, that is lower than the prescribed dose D, as a function of a variable B that cumulates the values (AD−D).

14 Claims, 3 Drawing Sheets

MEDICATION DELIVERY DEVICE

The present invention relates to a medication delivery device, in particular to an injection device for injecting medication through the skin of a patient.

More specifically, the present invention relates to a device comprising means for receiving a replaceable medication container, such as a cartridge, a control unit and means, controlled by the control unit, for delivering at least one dose of the medication contained in the medication container to a patient. Such a device is disclosed, for example, in WO 2005/077441.

A problem with such a known device resides in that the content of the medication container is rarely a multiple of the dose prescribed to the patient, as the dose generally varies from one patient to another and medication containers are standard components. Thus, after all the full doses contained in the medication container have been delivered, there is generally some medication left in the said container. This medication remainder cannot be used and, therefore, is thrown away by the patient with the medication container. This implies that medication is wasted. Over a high number of medication containers used, such a waste may be considerable.

The present invention aims at reducing this medication waste and provides, to this end, a medication delivery device as defined in appended claim 1, a method for determining medication doses as defined in appended claim 8 and a computer program as defined in appended claim 14, particular embodiments of the invention being defined in the appended dependent claims.

Other features and advantages of the present invention will be apparent from the reading of the following detailed description of preferred embodiments made with reference to the annexed drawings in which.

Figure 1:
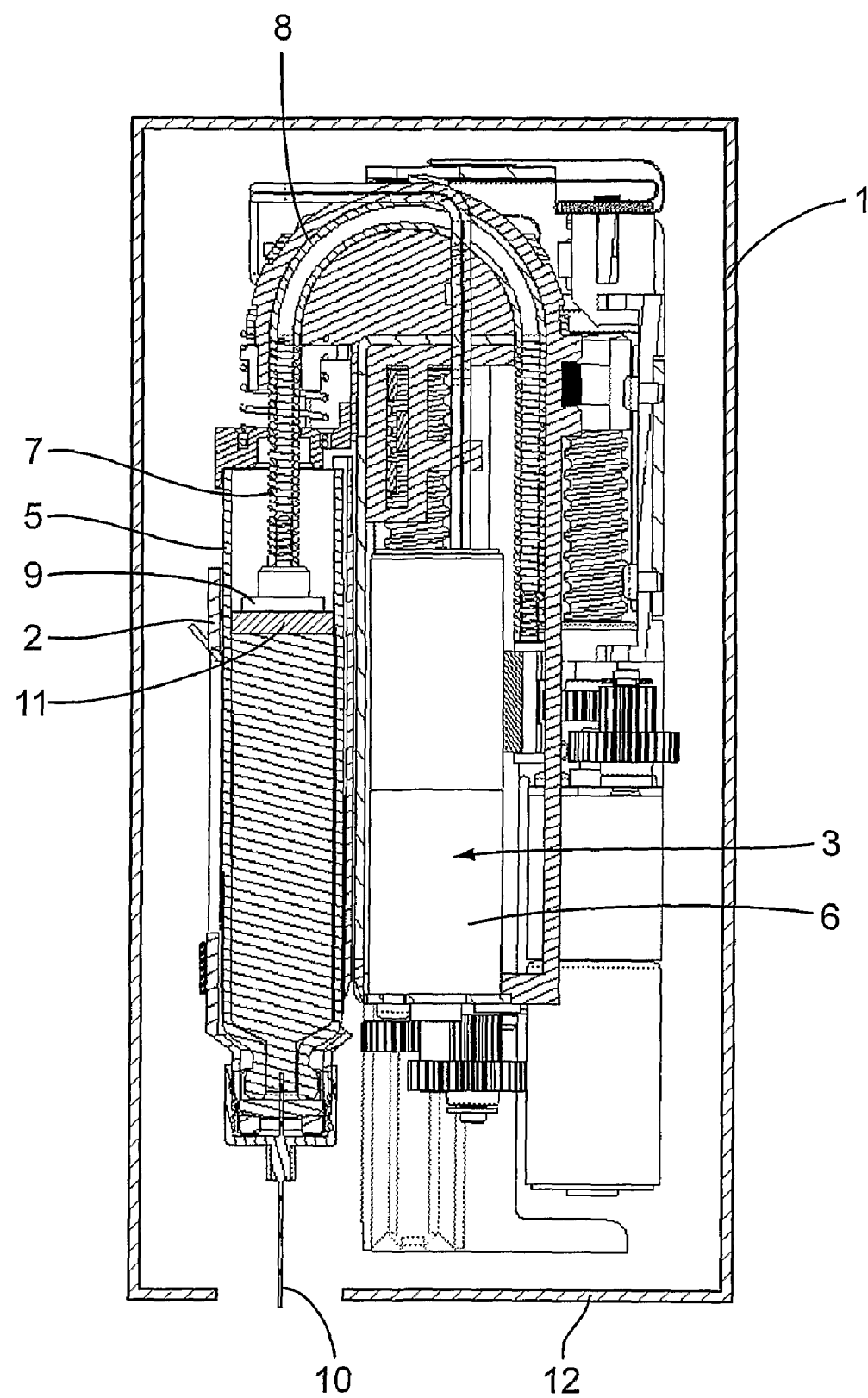
FIG. 1 is a section view of an electronic medication injection device according to the present invention.
Figure 2:
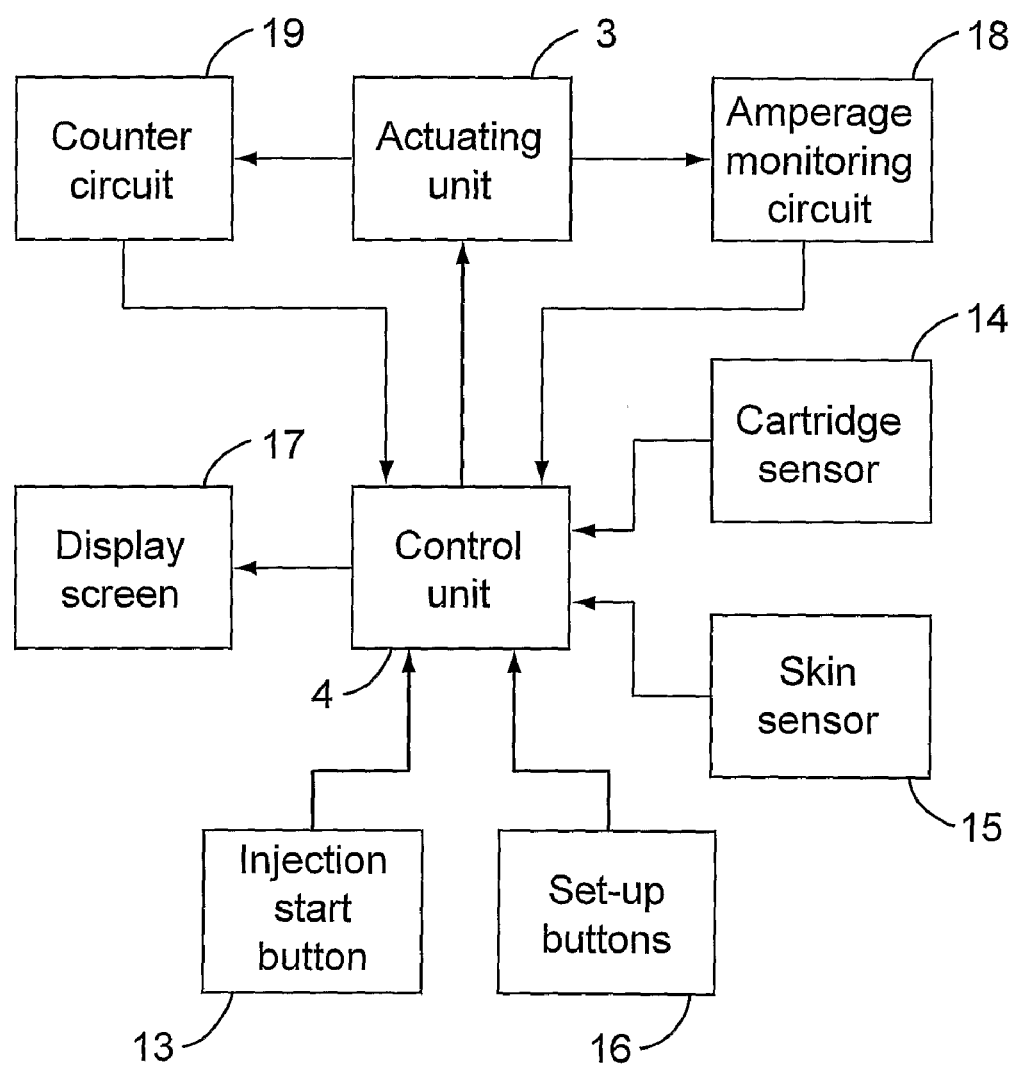
FIG. 2 is a block-diagram showing operation of a control unit for controlling the device of FIG. 1.

Referring to FIGS. 1 and 2, a hand-held electronic injection device according to the invention, for injecting liquid medication through the skin of a patient, comprises a hand-held housing 1 which accommodates a cartridge holder 2, an electromechanical actuating unit 3 and an electronic control unit 4. The cartridge holder 2 is designed to receive a replaceable cartridge 5 containing the liquid medication. The actuating unit 3 comprises an electric motor 6 and a piston rod 7 actuated by the motor 6. The piston rod 7 is in the form of an axially incompressible but laterally elastically deformable tube passing through a curved housing 8 and terminated by a pushing plate 9. After a cartridge 5 has been inserted into the cartridge holder 2 and a needle 10 has been attached to a lower end of the cartridge holder 2 so as to pierce the corresponding end of the cartridge 5, the piston rod 7 is axially displaced by the motor 6 so that the pushing plate 9 comes into contact with a piston 11 in the cartridge 5. Then, if predefined conditions are fulfilled, such as contact of the patient's skin with a bottom surface 12 of housing 1, the piston rod 7 will push the piston 11 to deliver one dose of medication through the needle 10 each time an injection start button 13 is pressed. Once the cartridge 5 is empty, or is considered to be empty, the piston rod 7 is retracted to allow replacement of the cartridge 5.

Referring to FIG. 2, the control unit 4, typically a microprocessor having an internal memory, receives signals from various sensors and buttons on the injection device, and controls the actuating unit 3 according to a program stored in the control unit 4. The sensors may include, in particular, a sensor 14 for detecting the presence of a cartridge 5 in the device and for reading information, such as a bar code, provided on the external wall of cartridge 5, and a sensor 15 for detecting a proximity or a contact of the patient's skin with the bottom surface 12. The buttons include the injection start button 13 and set-up buttons 16. The control unit 4 may also control the display of information for the patient or the physician on a display screen 17 provided on the injection device.

The construction of this medication injection device, in itself, is not part of the invention and, therefore, will not be described in further detail.

Figure 3:
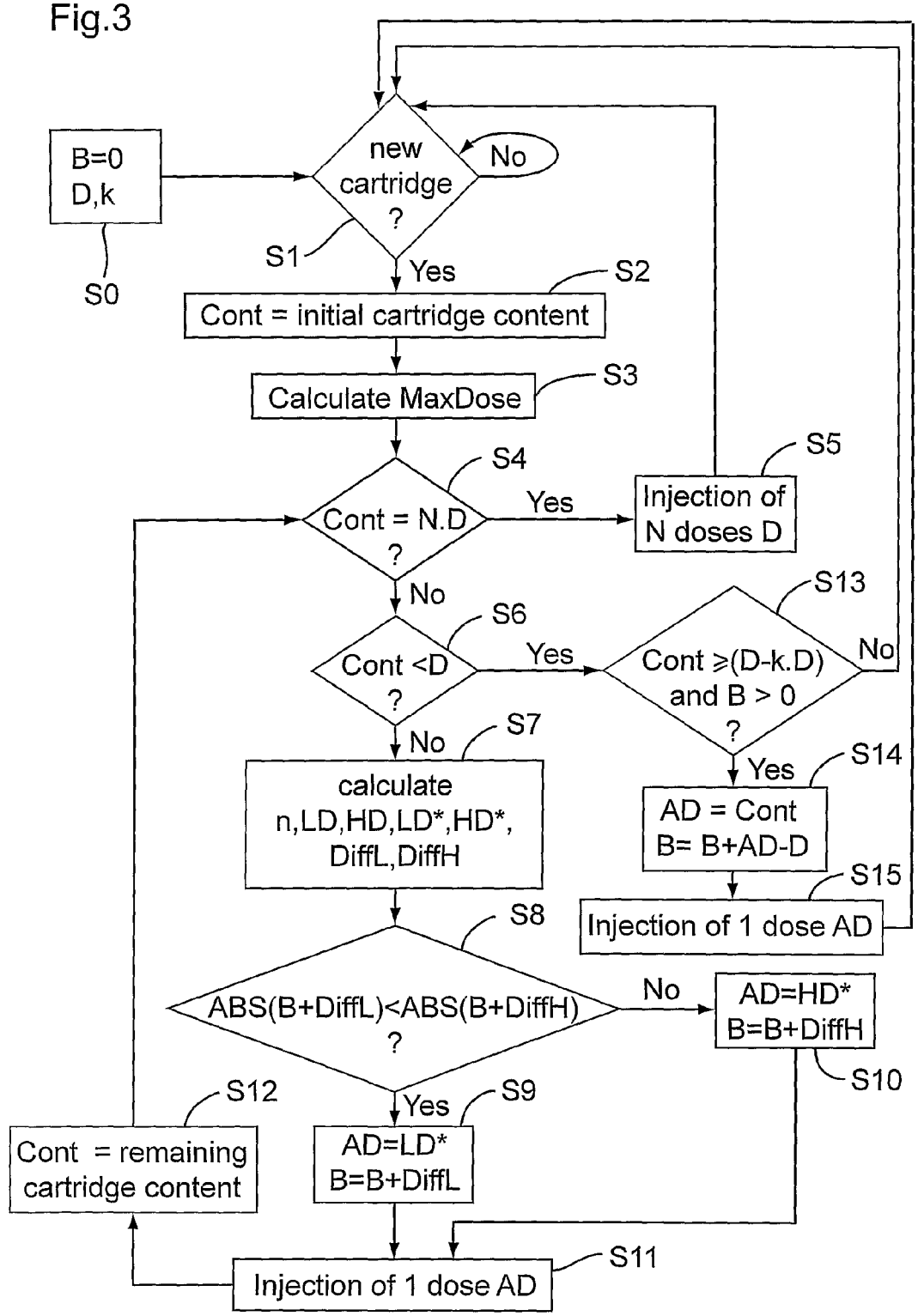
FIG. 3 shows an algorithm performed by the control unit of FIG. 2.

In accordance with the present invention, the program stored in the control unit 4 includes a subprogram for adjusting the medication dose to be delivered to the patient in order to reduce medication waste. The algorithm performed by this subprogram is shown in FIG. 3.

This algorithm starts by a step S0 in which a variable B is reset (the function of this variable will be explained later on) and a prescribed dose D, expressed for example in mg, and a predefined constant k, comprised between 0 and 1 and representing a dose accuracy, are stored in the control unit 4. The prescribed dose D and the dose accuracy k are typically provided to the control unit 4 by a physician via the set-up buttons 16.

In a following step S1, it is checked whether a cartridge 5 is inserted in the injection device. If no cartridge is present in the device, the algorithm waits until a cartridge is inserted and then goes to a step S2.

In step S2, a variable Cont, expressed for example in mg, and representing the current content of the cartridge 5 received in the device, i.e. the current amount of medication contained in the said cartridge, is given the value of the initial content of the cartridge 5. This initial cartridge content is, for example, pre-stored in the control unit 4, provided to the control unit 4 by the patient or the physician via the set-up buttons 16 or read by the sensor 14 on cartridge 5. Alternatively, the initial cartridge content may be determined by the injection device itself in the following manner: the piston rod 7 is brought into contact with the cartridge piston 11 from its known, retracted position; such a contact, which causes the amperage of motor 6 to increase, is detected by an amperage monitoring circuit 18; a counter circuit 19 counts the number of revolutions of the motor 6 to determine the distance covered by the piston rod 7 from its retracted position up to its contact with the cartridge piston 11, and thus the initial position of the cartridge piston 11 in the cartridge 5; from this initial position and the known dimensions of the cartridge 5, the initial cartridge content is then determined.

In a following step S3, a variable MaxDose is calculated as follows:

$$MaxDose = Conc \cdot MaxInjVol$$

where Conc is the concentration of the medication in the cartridge and MaxInjVol is a predetermined constant corresponding to the maximum volume that the injection device can inject in one injection. The values Conc and MaxInjVol are expressed, for example, in mg/ml and in ml respectively. The value Conc is for example pre-stored in the control unit 4, provided to the control unit 4 by the patient or the physician via the set-up buttons 16, or read by the sensor 14 on the cartridge 5.

In a following step S4, it is determined whether the current cartridge content Cont is a multiple of the prescribed dose D, i.e. is equal to the prescribed dose D multiplied by an integer number N not less than 1. If the answer is yes in step S4, the algorithm allows N injections of the prescribed dose D (step S5), injections that the patient will make according to an injection timing prescribed by the physician, and waits until these N injections are performed. Once these N injections have been performed, the control unit 4 informs the patient, via the display screen 17, that the cartridge 5 is empty and must be replaced. The algorithm then returns to step S1.

If the answer is no in step S4, it is determined in a step S6 whether the current cartridge content Cont is less than the prescribed dose D. If the answer is yes, the algorithm goes to a step S13 which will be described later on. If the answer is no, the algorithm goes to a step S7.

In step S7, the following variables are calculated:

$$n=\text{INT}(Cont/D)$$

$$LD=Cont/(n+1)$$

$$HD=Cont/n$$

$$LD^*=\max(LD,(D-k.D))$$

$$HD^*=\min(HD,\text{MaxDose},(D+k.D))$$

$$\text{Diff}L=(LD^*-D)$$

$$\text{Diff}H=(HD^*-D)$$

where INT is the integer part, max is the maximum value and min is the minimum value.

The variables LD and HD represent, respectively, a lower dose and a higher dose than the prescribed dose D. Unlike the prescribed dose, these lower and higher doses are dividers of the current cartridge content Cont. $LD^*$ is a lower dose that is equal to LD if LD is greater than a bottom value (D−k.D) and that is equal to (D−k.D) otherwise. $HD^*$ is a higher dose that is equal to HD if HD is smaller than two ceiling values, (D+k.D) and MaxDose, and that is equal to (D+k.D) or MaxDose otherwise. The dose accuracy k is selected by the physician as a function of the disease from which the patient suffers and of the patient himself. The ceiling value MaxDose is a technical restriction of the device.

In a following step S8, it is determined whether the absolute value of (B+DiffL) is smaller than the absolute value of (B+DiffH). If the answer is yes, an adjusted dose AD is set to be equal to the lower dose $LD^*$, and the variable B is given the new value (B+DiffL) (step S9). If the answer is no, the adjusted dose AD is set to be equal to the higher dose $HD^*$, and the variable B is given the new value (B+DiffH) (step S10).

In a following step S11, the algorithm allows one injection of the adjusted dose AD determined in step S9 or S10 and waits until this injection is performed. Once this injection has been performed, the algorithm gives to the variable Cont the value of the remaining cartridge content (step S12) and then returns to step S4.

Step S13, which is performed when the current cartridge content Cont is determined in step S6 to be less than the prescribed dose D, consists in determining whether the current cartridge content Cont is not less than the bottom value (D−k.D) and whether the variable B is greater than zero. If one or both of these conditions are not fulfilled, the patient is informed via the display screen 17 that the cartridge 5 must be replaced and the algorithm returns to step S1. If the two conditions set in step S13 are fulfilled, the adjusted dose AD is set to be equal to the current cartridge content Cont and the variable B is given the new value B+AD−D (step S14). The algorithm then allows one injection of the adjusted dose AD and waits until this injection is performed (step S15). Once this injection has been performed, the patient is informed via the display screen 17 that the cartridge 5 is empty and must be replaced, and the algorithm returns to step S1.

Steps S1 to S15 are carried out for each cartridge inserted in the injection device. So long as the prescribed dose D remains unchanged, the variable B is not reset, even if the injection device is switched off between two injections. If, at any moment, the prescribed dose D stored in the device is changed, the algorithm goes to step S0 where the variable B is reset.

The variable B represents a balance that cumulates the values (AD−D) as successive injections are carried out and successive cartridges are used in the device. In other words, the variable B represents the difference, at a given instant, between the amount of medication administered to the patient and the amount of medication that would have been administered if the dose had not been changed with respect to that prescribed. Such a difference may be positive or negative.

By determining the adjusted doses AD to be injected into the patient instead of the prescribed dose D based on the variable B, the algorithm as described above statistically reduces medication waste, i.e. reduces medication waste at least over a large number of injections performed. Medication waste W can be defined as follows:

$$W = \frac{\sum_i r_i}{\sum_i Cont_i}$$

where $r_i$ is the medication remainder in a given cartridge i after all possible dose injections have been performed for this cartridge, and $Cont_i$ is the initial content of cartridge i. In the present invention, the medication remainder $r_i$ is zero if the algorithm goes to step S5 or to step S15 for the cartridge i. The medication remainder $r_i$ is different from zero if in step S13 the current cartridge content Cont is determined to be less than (D−k.D) and/or the variable B is determined to be not greater than zero. One will understand that medication waste is more rapidly reduced if the dose accuracy k is great, i.e. near 1. If, on the other hand, the dose accuracy k is small, i.e. near 0, medication waste will be less rapidly reduced but the doses administered to the patient will remain closer to that prescribed.

One will further note that the decision rule used in step S8, involving the variable B, guarantees that the average dose administered to the patient converges to the prescribed dose D, i.e. that after a certain number of injections have been performed (using a certain number of cartridges), the average dose administered to the patient is substantially equal to the prescribed dose D. In many medical treatments indeed, such as the treatment of growth deficiency, the dose administered at each injection need not accurately correspond to that prescribed by the physician, provided that the average of the administered doses over a certain period, typically one or several weeks, is substantially equal to the prescribed dose. The present invention uses this medical tolerance to reduce medication waste.

Another property of the above algorithm is that the absolute value of the variable B is never greater than 50% of the prescribed dose D. Thus, the variation between the amount of medication received by the patient and the amount of medication that he/she should have received according to his/her medical prescription remains at any time limited.

Furthermore, this algorithm is particularly robust due to the fact that, in the main part S7 to S11 of the algorithm, an adjusted dose AD is calculated before each injection and not only once for each cartridge.

Although the decision rule used in step S8 is considered by the present inventors as being optimal for the rate of convergence of the average injected dose to the prescribed dose, it must be noted that other decision rules involving the variable B could be chosen. In a variant of the present invention, the lower dose LD* is selected as the adjusted dose AD if the value of variable B is positive and the higher dose HD* is selected as the adjusted dose AD if the value of variable B is negative or zero.

In a more general manner, it will be clearly apparent to those skilled in the art that modifications can be brought to the algorithm as described above without departing from the scope of the appended claims. For example:

- the steps S4 and S5 can be suppressed. In this case, the algorithm goes directly to step S6 after step S3 and step S12;
- the steps S13 to S15 can be suppressed. In this case, the algorithm returns directly to step S1 if the answer in step S6 is yes;
- in the cases where the physician allows a larger variation between the injected doses and the prescribed dose, and where no technical restriction exists as to the volume of medication that can be injected by the device in one injection, the dose accuracy k and the ceiling variable MaxDose can be suppressed from the algorithm.

The present invention has been described above in the context of an injection device for injecting medication through the skin of a patient. However, it is clearly apparent that the invention may apply to other medication delivery devices, for example to devices which provide the patient with appropriate doses of medication to be administered orally.

The invention claimed is:

1. A medication delivery device comprising means for receiving a replaceable medication container, a control unit and means, controlled by said control unit, for delivering at least one dose of the medication contained in said medication container to a patient, and means for determining an adjusted medication dose AD before each delivery of the medication contained in said medication container if the current content of the medication container is not a multiple of a prescribed dose D and is greater than the prescribed dose D, said adjusted medication dose AD being the dose to be delivered by said delivering means instead of the prescribed dose D during said medication delivery, said adjusted medication dose AD being determined by selecting one of a first dose, that is higher than the prescribed dose D, and of a second dose, that is lower than the prescribed dose D, as a function of a variable B that cumulates the values AD-D.

2. The medication delivery device according to claim 1, wherein the adjusted medication dose AD is the one, among the first and second doses, for which the absolute value of the variable B is lower.

3. The medication delivery device according to claim 1, wherein the adjusted medication dose AD is equal to the first dose if the variable B is negative and is equal to the second dose if the variable B is positive.

4. The medication delivery device according to claim 1 wherein the first dose is equal to (Cont/n) and the second dose is equal to (Cont/(n+1)), where n is equal to INT (Cont/D) and Cont is the current content of the medication container.

5. The medication delivery device according to claim 1 wherein the first dose is equal to the minimum of (Cont/n) and at least one ceiling value and the second dose is equal to the maximum of (Cont/(n+1)) and at least one bottom value, where n is equal to INT (Cont/D) and Cont is the current content of the medication container.

6. The medication delivery device according to claim 5, wherein said at least one ceiling value includes the value (D+k.D) and said at least one bottom value includes the value (D−k.D), where k is a predefined constant between 0 and 1.

7. The medication delivery device according to claim 1, including an electronic injection device designed to inject medication through the skin of a patient.

8. A method for determining medication doses, said method being performed by a control unit in a medication delivery device also comprising means for receiving a replaceable medication container and means controlled by said control unit, for delivering at least one dose of the medication contained in said medication container to a patient, comprising the steps: determining an adjusted medication dose AD before each delivery of the medication contained in said medication container if the current content of the medication container is not a multiple of a prescribed dose D and is greater than the prescribed dose D, said adjusted medication dose AD being the dose to be delivered by said delivering means instead of the prescribed dose D during said medication delivery, said adjusted medication dose AD being determined by selecting one of a first dose, that is higher than the prescribed dose D, and of a second dose, that is lower than the prescribed dose D, as a function of a variable B that cumulates the values AD-D.

9. The method according to claim 8, wherein the adjusted medication dose AD is the one, among the first and second doses, for which the absolute value of the variable B is lower.

10. The method according to claim 8, wherein the adjusted medication dose AD is equal to the first dose if the variable B is negative and is equal to the second dose if the variable B is positive.

11. The method according to claim 8, wherein the first dose is equal to (Cont/n) and the second dose is equal to (Cont/(n+D), where n is equal to INT (Cont/D) and Cont is the current content of the medication container.

12. The method according to claim 8, wherein the first dose is equal to the minimum of (Cont/n) and at least one ceiling value and the second dose is equal to the maximum of (Cont/(n+D) and at least one bottom value, where n is equal to INT (Cont/D) and Cont is the current content of the medication container.

13. The method according to claim 12, wherein said at least one ceiling value includes the value (D+k.D) and said at least one bottom value includes the value (D−k.D), where k is a predefined constant between 0 and 1.

14. A computer program executable by a control unit in a medication delivery device including means for receiving a replaceable medication container and means, controlled by said control unit, for delivering at least one dose of medication contained in said medication container to a patient, said code comprising an instructions code for performing the method defined in claim 8.

* * * * *